United States Patent
Im et al.

(10) Patent No.: US 9,741,119 B2
(45) Date of Patent: Aug. 22, 2017

(54) DISPLAY APPARATUS AND CONTROL METHOD THEREOF

(71) Applicant: SAMSUNG ELECTRONICS CO., LTD., Suwon-si (KR)

(72) Inventors: Sang-kyun Im, Seoul (KR); Cheon-seong Lee, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 220 days.

(21) Appl. No.: 14/580,535

(22) Filed: Dec. 23, 2014

(65) Prior Publication Data

US 2015/0178912 A1    Jun. 25, 2015

(30) Foreign Application Priority Data

Dec. 24, 2013  (KR) ........................ 10-2013-0162194

(51) Int. Cl.
| | |
|---|---|
| *G06T 7/00* | (2017.01) |
| *H04N 7/18* | (2006.01) |
| *G09B 19/00* | (2006.01) |
| *G06T 7/70* | (2017.01) |
| *G06F 19/00* | (2011.01) |

(52) U.S. Cl.
CPC ............ *G06T 7/004* (2013.01); *G06F 19/345* (2013.01); *G06T 7/0012* (2013.01); *G06T 7/70* (2017.01); *G09B 19/00* (2013.01); *H04N 7/183* (2013.01); *G06F 19/3437* (2013.01); *G06F 19/3487* (2013.01); *G06T 2207/30196* (2013.01); *G06T 2215/16* (2013.01)

(58) Field of Classification Search
CPC .......... H04N 7/183; G06T 2207/10004; G06T 2207/30196; G06T 2215/16
USPC .......................................................... 348/77
See application file for complete search history.

(56) References Cited

U.S. PATENT DOCUMENTS

| | | | |
|---|---|---|---|
| 2002/0151824 A1* | 10/2002 | Fischer | .................. A61B 5/103 600/595 |
| 2012/0266093 A1* | 10/2012 | Park | ...................... G06F 3/0486 715/769 |
| 2013/0058565 A1 | 3/2013 | Rafii et al. | |
| 2013/0185679 A1 | 7/2013 | Fretwell et al. | |
| 2014/0127658 A1* | 5/2014 | Rekimoto | .............. G09B 19/00 434/247 |
| 2014/0233814 A1* | 8/2014 | Ikeda | ..................... A61B 6/507 382/128 |

FOREIGN PATENT DOCUMENTS

KR    10-2013-0081596 A    7/2013

* cited by examiner

*Primary Examiner* — Hee-Yong Kim
(74) *Attorney, Agent, or Firm* — Sughrue Mion, PLLC (57) ABSTRACT

A display apparatus including a camera configured to capture a user's figure, a storage configured to store information about stress areas on a body in accordance with corresponding postures of a user, a processor configured to determine a user's posture from an image captured by the camera, determine a position of one or more stress areas on a body corresponding to the determined posture based on the stored information about the one or more stress areas on the body, and process a stress-related image, in which the determined one or more stress areas are marked on an image corresponding to a user's figure, and a display configured to display the stress-related image.

18 Claims, 8 Drawing Sheets

DISPLAY APPARATUS AND CONTROL METHOD THEREOF

CROSS-REFERENCE TO RELATED APPLICATION

This application claims priority from Korean Patent Application No. 10-2013-0162194, filed on Dec. 24, 2013 in the Korean Intellectual Property Office, the disclosure of which is incorporated herein by reference in its entirety.

BACKGROUND

Field

Apparatuses and methods consistent with exemplary embodiments relate to a display apparatus, which can process content data and display a content image based on the processed content data, and a control method thereof, and more particularly, to a display apparatus, which has a structure for offering a user, who views a content image, an environment for correcting his/her posture, and a control method thereof.

Description of the Related Art

An image processing apparatus, which processes image data to be finally displayed as an image, is classified and divided into a type that basically includes a display panel to display an image by itself based on the processed image signal, and a type that processes an image signal and outputs the processed image signal to another device without a display panel. The former type is generally called a display apparatus, and may include a television (TV), a monitor, an electric blackboard, etc., as an example.

The display apparatus, such as the TV, which can be easily found by a general user, displays images of various contents such as broadcasting images of various channels that suit a user's taste. When the display apparatus displays an image of a content desired by a user, s/he chooses to view the corresponding image. Here, a running time of an image is varied depending on the kind or characteristic of contents. For example, one episode of drama has a running time of about 40 minutes to 1 hour, and a movie has a running time of about 2 hours. If a user views the plurality of content images consecutively, for example, if s/he views two or more episodes of a drama one after another, a total running time of the image becomes longer.

While a user views an image reproduced and displayed for a long time, s/he may have a bad posture for a long time, or s/he may have the same posture for a long time even if the posture is good. This might not be good for a user's health, and therefore a user should correct his/her posture for himself/herself. However, a user may be unaware of his/her own posture if s/he concentrates on an image while viewing the image. Accordingly, it would be better if the display apparatus offers a user an environment for making him/her correct his/her own posture.

SUMMARY

According to an aspect of an exemplary embodiment, there is provided a display apparatus including: a camera configured to capture a figure of a user; a processor configured to determine a posture of the user from the image captured by the camera, determine a position of one or more stress areas on the body corresponding to the determined posture based on the stored information about the one or more stress areas on the body, and process a stress-related image, in which the determined one or more stress areas are marked on an image corresponding to a figure of the user; and a display configured to display the stress-related image.

The storage may be configured to store information about one or more relaxing areas on the body in accordance with the corresponding postures, and to process the one or more stress areas and the one or more relaxing areas to be marked on the stress-related image.

The processor may be configured to process the one or more stress areas and the one or more relaxing areas to be different in color on the stress-related image.

The processor may be configured to process the one or more stress areas and the one or more relaxing areas to be different in contrast on the stress-related image.

The processor may be configured to process the one or more stress areas and the one or more relaxing areas to be different in brightness on the stress-related image.

The display may be configured to display a content image corresponding to a predetermined content together with the stress-related image.

The processor may be configured to determine the posture of the user while the content image is being displayed.

The processor may be configured to adjust the stress-related image to become larger as time elapses while a user stays in one posture, and return the stress-related image to an original size if it is determined that the user changes the posture while the stress-related image is enlarged.

The processor may be configured to process the stress area to be expanded on the stress-related image as time elapses while the user stays in one posture.

According to an aspect of another exemplary embodiment, there is provided a method of controlling a display, the method including: capturing a figure of a user with a camera; determining a posture of the user from an image captured by the camera, and determining a position of one or more stress areas on a body corresponding to the determined posture based on information previously stored about the one or more stress areas on the body, in accordance with corresponding postures of the user; and displaying a stress-related image, in which the determined one or more stress areas are marked on an image corresponding to the user's figure, on the display.

The determining the one or more stress areas on the body corresponding to the determined posture may include determining one or more relaxing areas on the body corresponding to the determined posture based on information previously stored about the one or more relaxing areas on the body in accordance with the corresponding postures; and the displaying the stress-related image may include displaying the one or more stress areas and the one or more relaxing areas on the stress-related image.

The displaying the one or more stress areas and the one or more relaxing areas may include displaying the one or more stress areas and the one or more relaxing areas to be different in color on the stress-related image.

The displaying the one or more stress areas and the one or more relaxing areas may include displaying the one or more stress areas and the one or more relaxing areas to be different in contrast on the stress-related image.

The displaying the one or more stress areas and the one or more relaxing areas may include displaying the one or more stress areas and the one or more relaxing areas to be different in brightness on the stress-related image.

The method may include displaying a content image corresponding to a predetermined content, and the displaying the stress-related image may include displaying the stress-related image together with the content image.

The determining the posture of the user may include determining the posture of the user while the content image is being displayed.

The displaying the stress-related image may include adjusting the stress-related image to become larger as time elapses while the user stays in one posture, and returning the stress-related image to an original size if it is determined that the user changes the posture while the stress-related image is enlarged.

The displaying the stress-related image may include expanding the stress area on the stress-related image as time elapses while a user takes one posture.

According to an aspect of another exemplary embodiment, there is provided an apparatus including a camera configured to capture a shape of a user, a processor configured to determine a posture of the user according to the captured shape of the user, and determine one or more stress areas of the user according to the determined posture of the user.

The processor may be configured to: process a stress-related image, in which the determined one or more stress areas are marked on an image corresponding to a figure of the user; and output the stress-related image to an external device.

The external device may be a display configured to display a content image corresponding to a predetermined content, and the stress-related image.

The processor may be configured to determine one or more relaxed areas of the user according to the posture of the user, and the display may be configured to display an image of the user identifying the one or more relaxed areas of the user.

The determining the one or more stress areas may include searching a database of stored postures to find the stored posture that is similar to the posture of the user.

BRIEF DESCRIPTION OF THE DRAWINGS

The above and/or other aspects will become apparent and more readily appreciated from the following description of exemplary embodiments, taken in conjunction with the accompanying drawings, in which.

DETAILED DESCRIPTION OF EXEMPLARY EMBODIMENTS

One or more exemplary embodiments will be described in detail with reference to accompanying drawings. In the following exemplary embodiments, only elements directly related to exemplary embodiments will be described, and descriptions about the other elements may be omitted. However, it will be appreciated that these other elements, the descriptions of which are omitted, may be necessary to realize the apparatus or system according to one or more exemplary embodiments.

Figure 1:
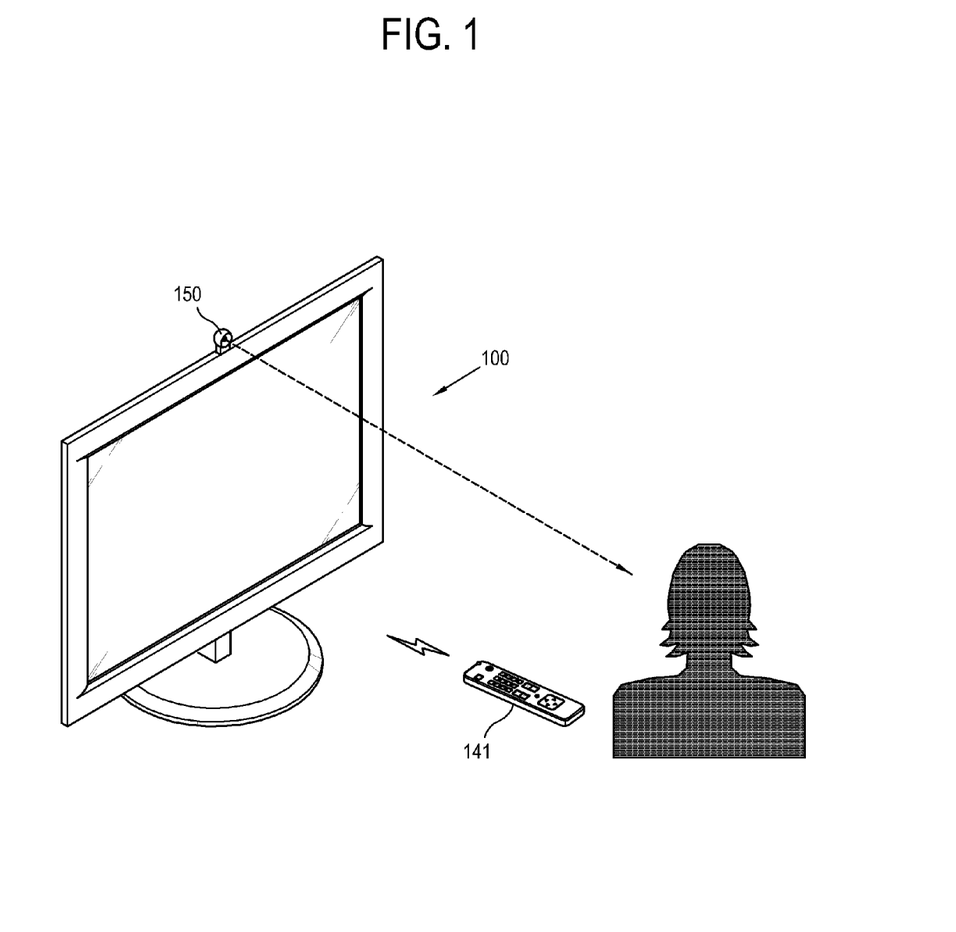
FIG. 1 illustrates an example of a display apparatus according to an exemplary embodiment.

FIG. 1 illustrates a display apparatus 100 according to an exemplary embodiment.

As illustrated in FIG. 1, the display apparatus 100 in the present exemplary embodiment processes image data of a content received from an exterior source, or stored therein, and displays an image corresponding to the content. In this exemplary embodiment, the display apparatus 100 is achieved by a TV, but is not limited thereto. Alternatively, there may be various types of the display apparatus capable of processing image data and displaying an image based on the image data, e.g., monitor, personal computer (PC), laptop computer, portable device, etc.

Furthermore, it is understood that one or more other exemplary embodiments are not limited to a display apparatus. For example, according to another exemplary embodiment, there may be an image processing apparatus (e.g., set-top box, audio/video receiver, storage device, standalone device, etc.) that outputs a display image to an external device.

One or more users may sit or stand in front of the display apparatus 100, and the users may view an image displayed on the display apparatus 100. The display apparatus 100 provides various user interface environments, i.e., user input/recognition structures, for allowing a user to control operations of the display apparatus 100.

For example, the user interface environment may include various kinds of function buttons, touch pads, a display, etc., and also may include a remote controller 141, separated from the display apparatus 100, and a camera 150 for videoing and photographing a user and external environments of the display apparatus 100. Of course, such environments for the user input interface provided in the display apparatus 100 are not limited to the above examples, and an input structure not described herein may be additionally provided in the display apparatus 100.

The display apparatus 100 can analyze an image taken by the camera 150. For example, the display apparatus 100 may determine a user's figure or shape presented within each image frame of the photographed image, thereby specifying a user's posture in a certain image frame. The display apparatus may also use a user's partial figure or shape presented within an image frame in order to determine a user's posture. In addition, the display apparatus 100 can perform various operations in accordance with analysis results. For example, the display apparatus 100 may analyze a user's posture during a predetermined period of time, determine what motion a user makes, and may perform a preset function corresponding to the specified motion.

In particular, the display apparatus 100 in this embodiment may determine a user's posture and display a user's body condition, thereby providing an environment for allowing a user to correct his/her own posture by him/herself. Details about this will be described.

Below, elements of an exemplary display apparatus 100 will be described.

Figure 2:
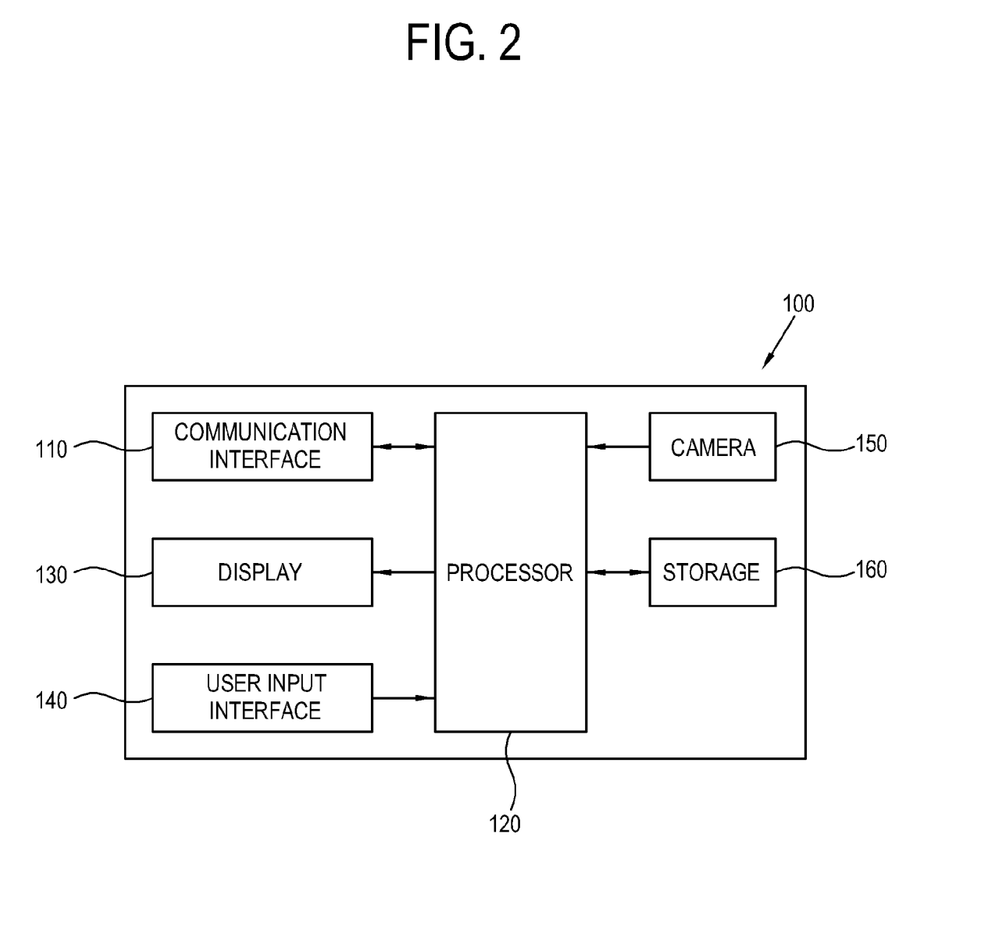
FIG. 2 is a block diagram illustrating an exemplary display apparatus of FIG. 1.

FIG. 2 illustrates a block diagram of an exemplary display apparatus 100 of FIG. 1.

As illustrated in FIG. 2, the display apparatus 100 may include a communication interface 110 to communicate with an exterior source to transmit and receive data/signal, a processor 120 to process data received in the communication interface 110, in accordance with a preset process, a display 130 to display an image based on image data, if the data processed by the processor 120 is image data, a user input interface 140 to receive a user's input, a camera 150 to photograph the external environments of the display apparatus 100, and a storage 160 to store data/information.

The communication interface 110 transmits and receives data so that the display apparatus 100 can interactively communicate with an external device, such as a server, or the like. The communication interface 110 connects with the external device through a wire, or wirelessly by a broadband/local area network, or a local connection method in accordance with preset communication protocols.

The communication interface 110 may have connection ports for respective devices, or an assembly of connection modules. In other words, the protocol for the connection or the external device to be targeted for the connection is not limited to any one kind or type. The communication interface 110 may be built-in to the display apparatus 100, or it may be partially, or entirely, provided in the form of an Add-on or Dongle to the display apparatus 100.

The communication interface 110 transmits and receives signals in accordance with protocols designated to the connected devices. Thus, the communication interface 110 can transmits and receives a signal based on an individual connection protocol with regard to the connected device. In the case of the image data, the communication interface 110 may transmit and receive a signal based on various standards, such as radio frequency (RF), composite/component video, super video, Syndicat des Constructeurs d'Appareils Radiorécepteurs et Téléviseurs (SCART), high definition multimedia interface (HDMI), DisplayPort, unified display interface (UDI), wireless HD, etc.

The processor 120 may perform various processes with regard to data/signals received in the communication interface 110. If the communication interface 110 receives the image data, the processor 120 may perform an image processing process with regard to the image data, and the processed image data may be output to the display 130 so that an image based on the image data can be displayed on the display 130. If the signal received in the communication interface 110 is a broadcasting signal, the processor 120 may extract an image, sound, and supplementary data from a broadcasting signal tuned to a certain channel, and control the image to have a preset resolution and be displayed on the display 130.

The image processing performed by the processor 120 is not limited to the above, and may, for example, include decoding, corresponding to an image format of image data; de-interlacing for converting an interlaced type of image data into a progressive type, scaling for adjusting image data to have a preset resolution, noise reduction for enhancing image quality, detail enhancement, frame refresh rate conversion, etc.

The processor 120 may perform various processes in accordance with the kinds, characteristics, etc., of data, and thus the process to be performed by the processor 120 is not limited to image processing. Further, the data to be processed by the processor 120 is not limited to the data/signals received in the communication interface 110. For example, if a control command corresponding to a user's control is received through the user input interface 140, the processor 120 may perform a preset operation or function in response to the corresponding control command.

The processor 120 may be achieved by a system-on-chip (SOC), where various functions are integrated, or an image processing board, where individual chipsets for independently performing each process are mounted onto a printed circuit board, and is internally provided in the display apparatus 100.

The display 130 displays an image based on an image signal/image data processed by the processor 120. The display 130 may be achieved by various types, such as liquid crystal, plasma, a light-emitting diode, an organic light-emitting diode, a surface-conduction electron-emitter, a carbon nano-tube, a nano-crystal, a cathode ray tube (CRT), an active-matrix organic light-emitting diode (AMOLED), a Super AMOLED, etc., without limitation.

The display 130 may include additional elements in accordance with its types. For example, if the display 130 employs the liquid crystal, the display 130 includes a liquid crystal display (LCD) panel, a backlight unit emitting light to the LCD panel, and a panel driving substrate for driving the LCD panel.

The user input interface 140 transmits various preset control commands, or information, to the processor 120, in accordance with a user's control or input. The user input interface 140 processes various events generated by a user, in accordance with a user's intention, and transmits it to the processor 120. The event generated by a user may be given in various forms, and may, for example, include a user's control on the remote controller 141 (refer to FIG. 1), or a user's speech, etc.

The camera 150 videos the external environments of the display apparatus 100, in particular, a user's figure, and transmits the videoed result to the processor 120. In this exemplary embodiment, the camera 150 provides the processor 120 with a two-dimensional image obtained by videoing a user's figure, so that the processor 120 can specify a user's shape and figure within the image frame of the videoed image.

The storage 160 stores a variety of data under control of the processor 120. The storage 160 may be achieved by a nonvolatile memory such as a flash memory, a hard disk drive, or the like, to preserve data regardless of whether system power is on or off. The storage 160 may be accessed by the processor 120 to read, record, modify, delete and update the previously stored data.

With this structure, the display apparatus 100 processes predetermined content data and displays a content image to be viewable by a user.

A playback time of one content may be more than 1 hour in accordance with the kinds of content, and a total playback time may be more than several hours if a plurality of contents is continuously played back.

While the image is viewed for a long time, a user may take various postures. However, a certain posture may be ergonomically bad to a human. Such a bad posture may, for example, include postures where one leg is crossed with the other leg, a chin is rest on one hand, a head is tilted, a front of a body is twisted to one side without facing the image, and so on. In general, if a user takes a posture where his/her body leans toward either the left or right side, it is regarded as a model of bad posture.

Further, if a user does not change a certain posture for a long time, even if the posture is not ergonomically bad to a human, this may be also bad to the human. When a user maintains and does not change a particular posture, s/he may be particularly interested or immersed in an image being displayed on the display apparatus 100.

Thus, the display apparatus 100 provides a user with environments so that s/he can easily recognize his/her unconscious viewing habit and correct a posture for him/herself. This will be described below.

Figure 3:
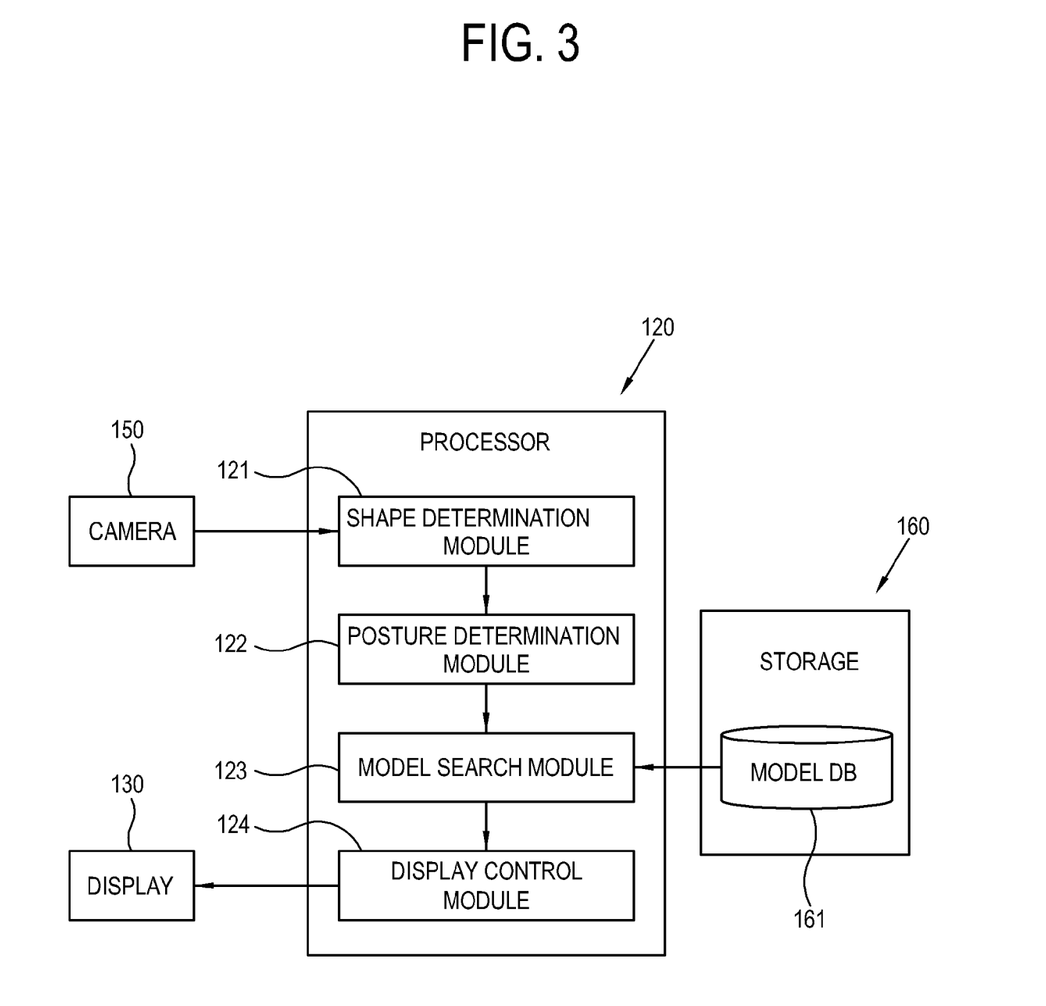
FIG. 3 is a block diagram illustrating an operation principle of an exemplary display apparatus of FIG. 1.

FIG. 3 is a block diagram illustrating an operation principle of the display apparatus 100 according to an exemplary embodiment.

As illustrated in FIG. 3, the processor 120 includes a shape determination module 121, for determining a user's shape within an image frame of a user's videoed image, taken by the camera 150; a posture determination module 122, for determining a user's posture based on the determined shape of the user; a model search module 123 for searching posture model information corresponding to the determined posture of the user from a previously stored model database (DB) 161; and a display control module 124 for controlling the display 130 to display, to a user, a corresponding image that shows a body's stress area according to a user's posture, based on the searched posture model information.

The foregoing respective blocks or modules 121, 122, 123, and 124, of the processor 120, were divided and named for convenience in accordance with their operations or functions, and thus an exemplary embodiment is not limited thereto. When the processor 120 is achieved according to an exemplary embodiment, it may be not divided like the modules 121, 122, 123 and 124 according to this exemplary embodiment. Alternatively, the processor 120 may perform all the operations in sequence, or some of the modules 121, 122, 123, and 124, may be integrated. In addition, each of the modules 121, 122, 123, and 124, may be achieved by hardware, software, or a combination of hardware and software.

The shape determination module 121 determines an image area corresponding to a user within an image frame of a user's videoed image taken by the camera 150. If an image area corresponding to a user is a foreground and the other area is a background within the image frame, the shape determination module 121 determines the foreground within the image frame. Further, the shape determination module 121 determines parts such as a head, a face, arms, legs, etc., that constitute a user's body within the foreground.

The posture determination module 122 may determine a user's posture based on the shape of the user body determined by the shape determination module 121. The posture determination module 122 may employ various modeling methods to determine a user's posture, and thus, an exemplary embodiment is not limited thereto. For example, a model about the plurality of postures modeled corresponding to the respective shapes of the user body may be previously designated, and stored in the display apparatus 100. The posture determination module 122 may specify one model, among the plurality of previously stored posture models, based on information about the shapes of the head, the body, two arms and two legs and relative positions thereof.

The model search module 123 searches and acquires information about a stress area/part of the body corresponding to a user's posture, determined by the posture determination module 122, from the model DB 161, previously stored in the storage 160. Further, the model search module 123 may search information about stress areas and relaxing areas of the body, corresponding to a user's posture, determined by the posture determination module 122 from the model DB 161.

The stress area indicates a user's body part that is relatively stressed when s/he has a certain posture, and the relaxing area indicates a user's body part that is relatively relaxed when s/he has a certain posture. The stress area and the relaxing area are relatively defined, and thus, shown in any posture, even when a user takes the corresponding posture.

The model DB 161 includes information about the stress and relaxing areas of the body according to the plurality of preset postures of a user. Such information stored in the model DB 161 may be derived from and designated by data accumulated through medical experiments, and there are various examples of the information without being limited to this exemplary embodiment.

For instance, assume that a user takes a posture where s/he sits on a chair looking straight ahead and keeps hands on his/her lap while straightening his/her back. When a user takes this posture, a user's shoulder, arms and legs, etc., are relatively relaxed, but his/her waist is relatively stressed. Thus, the relaxing area in the corresponding posture includes a user's shoulder, arms, legs, etc., and the stress area in the corresponding posture includes his/her waist.

Alternatively, assume that a user takes a posture where s/he leans his/her body leftward while supporting his/her left arm on an armrest. When a user takes this posture, a user's right shoulder, right arm, etc., are relatively relaxed, but his/her neck, left shoulder, left arm, waist, etc., are relatively stressed. Thus, the relaxing area in the corresponding posture includes a user's right shoulder, right arm, etc., and the stress area in the corresponding posture includes his/her neck, left shoulder, left arm, waist, etc.

As such, various pieces of experimental data are accumulated to build the model DB 161. The model search module 123 can search from the model DB 161 information about where the stress area and the relaxing area are positioned in a user's body in accordance with the determined posture of him/her.

If the model search module 123 acquires at least one piece of information between the stress area and the relaxing area corresponding to a user posture, the display control module 124 displays an image based on the acquired information, thereby offering the information to a user.

The display control module 124 may employ various methods for displaying an image based on the information about the stress and relaxing areas corresponding to the user posture.

Figure 4:
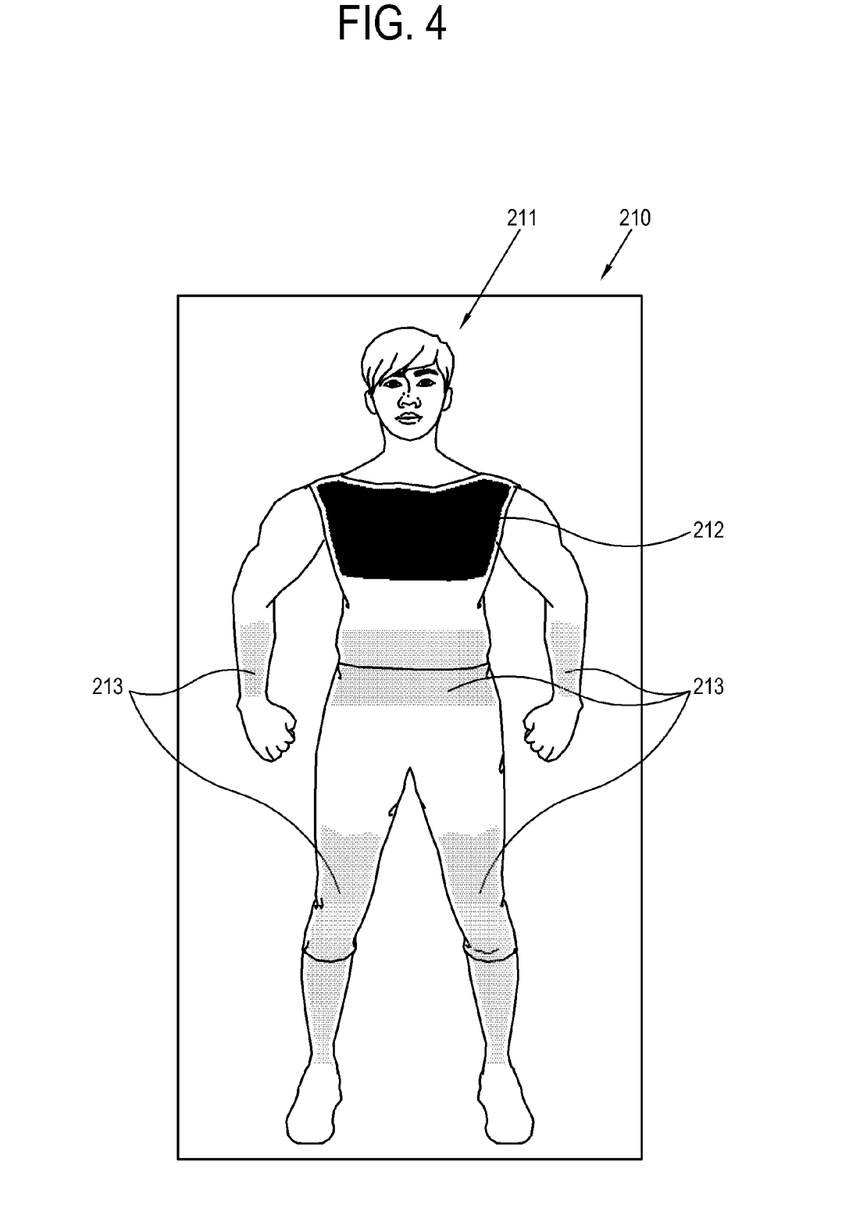
FIG. 4 illustrates an image showing a stress area corresponding to a certain posture, displayed on an exemplary display apparatus of FIG. 1.

FIG. 4 illustrates an example of an image 210 showing a stress area corresponding to a certain posture.

As shown in FIG. 4, the display apparatus 100 displays an image 211 corresponding to a user's figure.

The image 211 corresponding to a user's figure may be an actual image obtained by photographing a user or a preset separate image corresponding to a user's shape. Further, the image corresponding to a user's figure may have the same posture as a user's posture at a point of determination time, or one fixed posture. In addition, the image 211 corresponding to a user's figure may be a two-dimensional image or a three-dimensional image.

In this exemplary embodiment, the image 211 corresponding to a user's figure is represented as the two-dimensional image corresponding to a user's shape having the fixed posture, but it is not limited thereto, and may be varied depending on design methods.

As described above, in FIG. 4, the display apparatus 100 marks the stress area 212 and the relaxing area 213 at the specified positions on the image 211 corresponding to a user's figure if the positions of the stress area 212 and the relaxing area 213 corresponding to a user's posture at the current point of time are specified on the body. Thus, the display apparatus 100 displays an image 210 marked with the stress area 212 and the relaxing area 213 corresponding to a user's posture at the current point of time.

In other words, the display apparatus 100 allows a user to recognize such an image 210 so that he/she can easily determine where the stress area 212 is positioned in the current posture taken by him/her. Further, the display apparatus 100 may guide a user to easily change his/her posture based on the determined stress area 212.

In this exemplary embodiment, the image 210 is marked with both the stress area 212 and the relaxing area 213, but it is not limited thereto. Alternatively, the image 210 may be marked with only the stress area 212.

In addition, the stress area 212 and the relaxing area 213 in this exemplary embodiment have clear boundaries to be distinguished from each other, but it is not limited thereto. Alternatively, gradation may be reflected between the stress and relaxing areas 212 and 213 and the other areas in accordance with difference in a stress level. The difference in the stress level may be previously defined in the model DB (161, refer to FIG. 3).

Within the image 210, the stress area 212 and the relaxing area 213 may be distinguished by various methods. As one of the methods, the display apparatus 100 may make the stress area 212 and the relaxing area 213 different colors. For example, the display apparatus 100 may mark the stress area 212 with red and the relaxing area 213 with blue.

In addition, the display apparatus 100 may make the stress area 212 and the relaxing area 213 be different in contrast. For example, the display apparatus 100 may mark the relaxing area 213 with white or bright grey, and the stress area 212 with black or dark grey.

Further, the display apparatus 100 may make the stress area 212 flicker so that a user can easily recognize the corresponding part.

Furthermore, the display apparatus 100 may make the stress area 212 and the relaxing area 213 be different in brightness. For example, the display apparatus 100 may mark the stress area 212 with relatively high brightness, and the relaxing area 213 with relatively low brightness.

Figure 5:
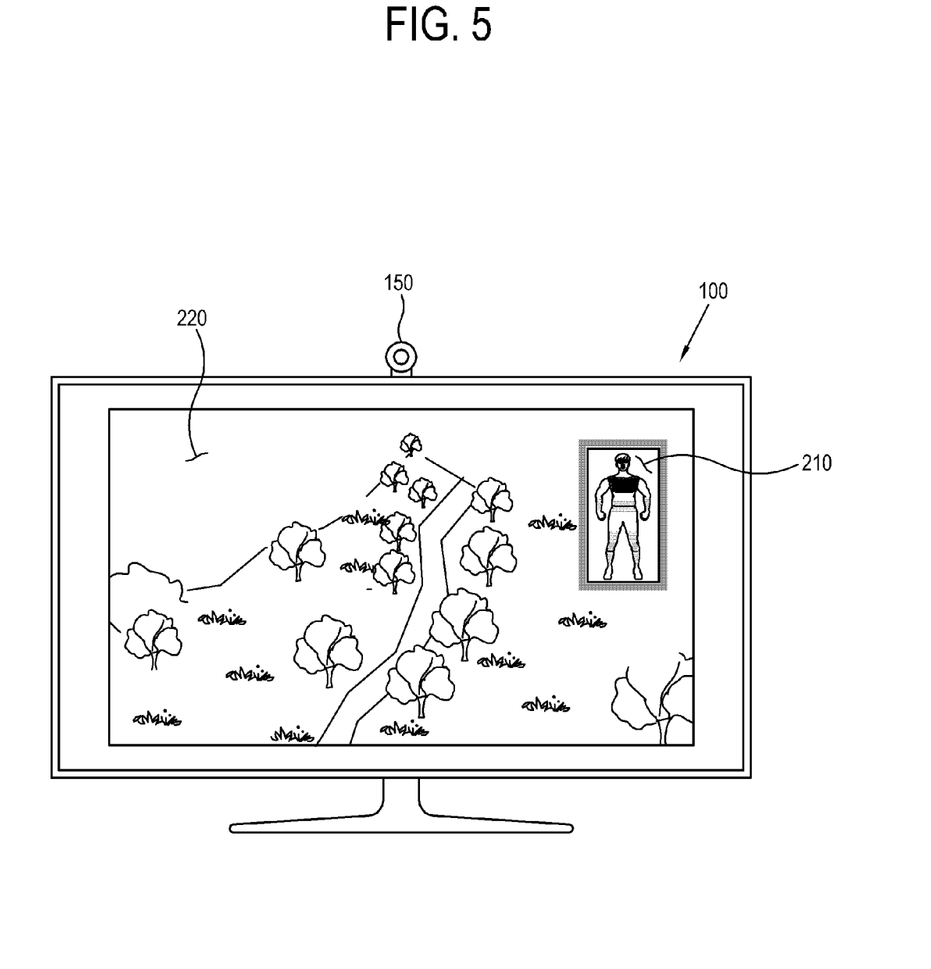
FIG. 5 illustrates that the display apparatus of FIG. 1 displays a content image together with an image showing a stress area with regard to a certain posture.

FIG. 5 illustrates an example where the display apparatus 100 displays a content image 220 together with an image 210 showing a stress area with regard to a certain posture.

As shown in FIG. 5, the display apparatus 100 processes predetermined content data and displays the content image 220. While the content image 220 is displayed, the display apparatus 100 videos a user's figure through the camera 150 and specifies the stress area on the body in accordance with a user's posture as described above.

The display apparatus 100 displays the content image 220 together with the image 210 marked with the specified stress area. The display apparatus 100 may pop up the image 210 of the stress area to be overlaid with the content image 220. Alternatively, the display apparatus 100 may divide the whole display screen into two regions, and respectively display the stress area image 210 and the content image 220 in the divided regions.

Therefore, a user may get information about his/her own posture through the image marked with the stress area while viewing the content image 220.

Figure 6:
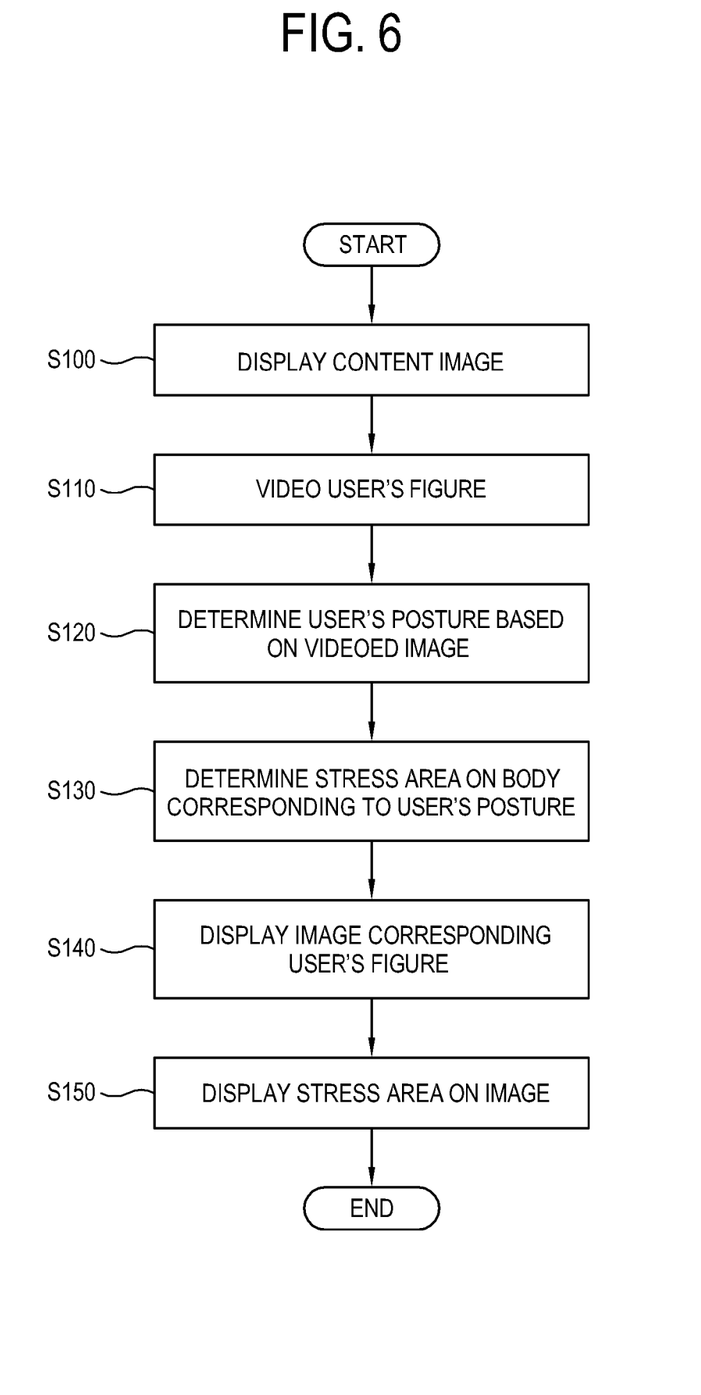
FIG. 6 is a flowchart illustrating a control method of an exemplary display apparatus of FIG. 1.

FIG. 6 is a flowchart showing a control method of the display apparatus 100.

As shown in FIG. 6, the display apparatus 100 displays a content image at operation S100.

At operation S110, the display apparatus 100 videos a user's figure while displaying the content image. At operation S120, the display apparatus 100 determines a user's current posture based on the videoed image. At operation S130, the display apparatus 100 determines the stress area in accordance with a user's posture.

At operation S140, the display apparatus 100 displays an image corresponding to a user's figure. At operation S150, the display apparatus 100 marks a stress area on the image corresponding to a user's figure.

The operations S120 to S150 are performed on the assumption that the operation S100 proceeds. That is, the display apparatus 100 determines a user's posture and determines and marks the stress area while displaying the content image. This is because the information is provided in order to correct a posture of a user who is viewing a content image.

Figure 7:
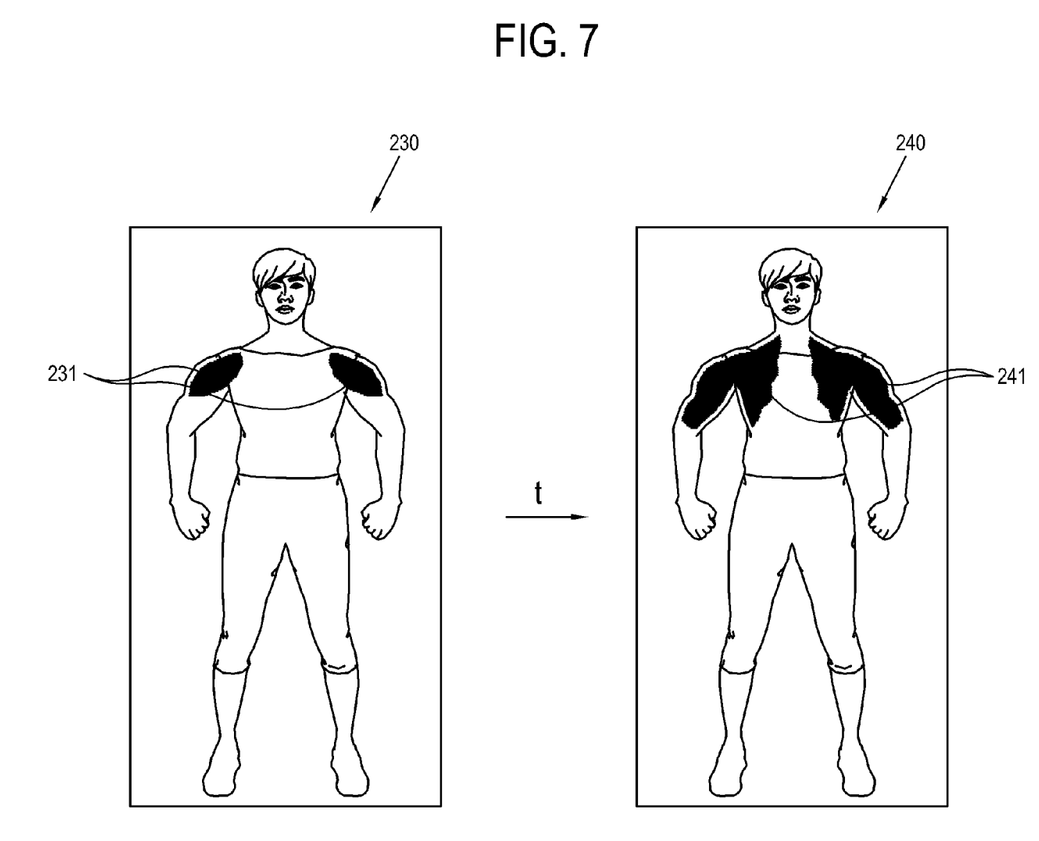
FIG. 7 illustrates that an image may be varied in a stress area according to an exemplary embodiment.

FIG. 7 shows an example that an image 230, 240 is varied in a stress area according to another exemplary embodiment.

As shown in FIG. 7, assume that an image 230 is marked with a stress area 231 according to a user's posture at a first point in time, and the stress area 231 on the image 230 corresponds to both shoulders of the body.

If a user continuously maintains the same posture as that at the first point in time, even at a second point in time after time t elapses from the first point of time, an image 240 according to a user's posture at the second point in time is marked with a stress area 241 corresponding to both shoulders of the body like that at the first point of time.

However, since muscles and nerves are connected to each other in a human's body, the stress area 231 of one posture gradually becomes larger if a user continuously maintains the corresponding posture. For instance, the posture initially having the stress area 231 at both shoulders is continuously maintained, the stress area 241 expands toward a back of a neck, arms and an upper body with respect to both shoulders of the body.

Taking this point into account, the display apparatus 100 displays the stress area 241 on the image 240 at the second point of time to be larger than the stress area 231 on the image 230 at the first point of time if it is determined that a user maintains one posture from the first point of time to the second point of time. As time elapses, the stress area may become larger and larger.

A direction and degree of expanding the area according to the elapsed time may be determined by various methods based on the data accumulated by applying many experiments to the body.

Figure 8:
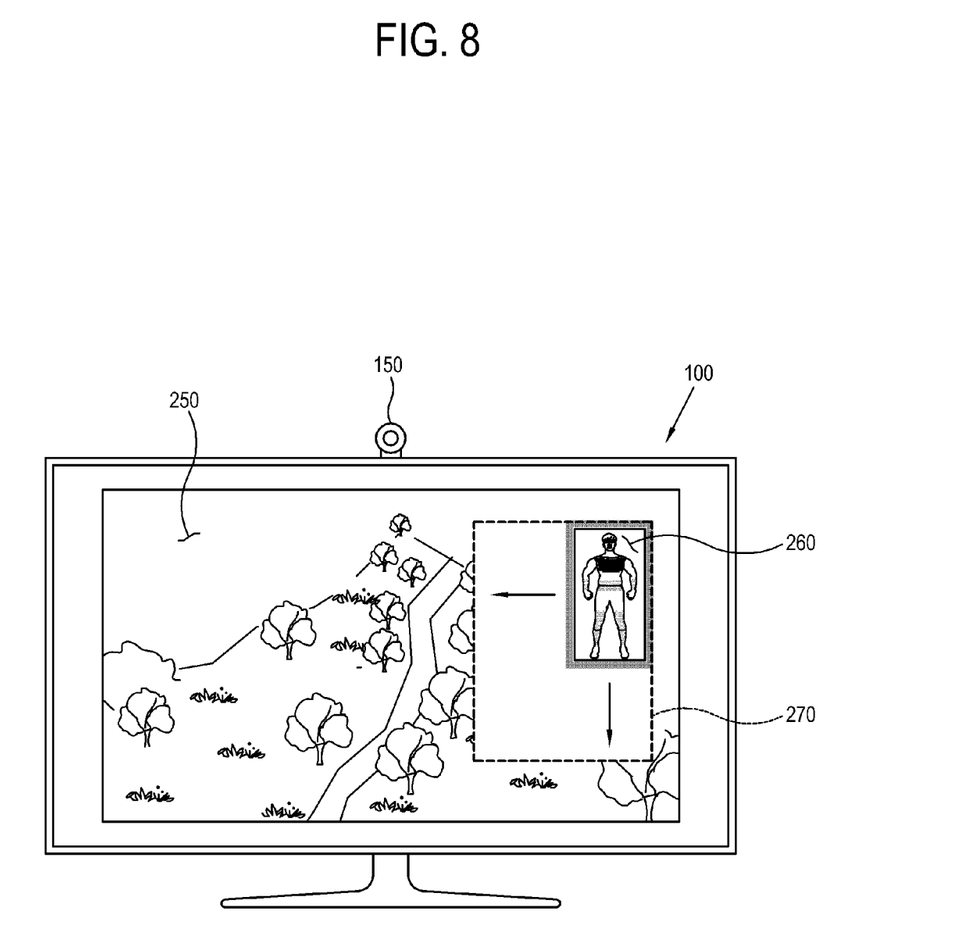
FIG. 8 illustrates a display method for a stress-related image according to an exemplary embodiment.

FIG. 8 shows an example of a display method for a stress-related image 260, 270 according to another exemplary embodiment.

As shown in FIG. 8, the display apparatus 100 videos a user's figure through the camera 150 while displaying a content image 250, and displays the stress-related image 260 according to the current posture to be overlaid with the content image 250. A method of displaying the stress-related image 260 may be achieved as mentioned in the foregoing exemplary embodiments, and thus detailed descriptions will be omitted.

The display apparatus 100 sets the size of the stress related image 270 at the second point of time to be larger than that at the first point of time, if it is determined that a user maintains the posture at the first point of time even at the second point of time after a preset time elapses from the first point of time at which the stress-related image 260 is displayed. That is, the display apparatus 100 adjusts the stress-related image 260, 270 to become larger if it is determined that a user's posture is not changed within the preset time.

On the other hand, the display apparatus 100 returns the stress-related image to an original size if it is determined that a user's posture is changed after displaying the stress-related image 270.

Thus, the display apparatus 100 may guide a user to correct his/her own posture.

Also, while the above-described exemplary embodiments refer to capturing an image of a figure or shape of a user, it is understood by a person of ordinary skill in the art that the disclosure is not limited to capturing an image of an entire user. For example, exemplary embodiments may involve capturing images of only a part or portion of a user, e.g., arms, legs, shoulders, head, hands, feet, etc. The captured image of a portion of a user can be used to determine a posture of a user, and in all other aspects of the exemplary embodiments.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses can include circuitry, a processor, a microprocessor, etc., and may execute a computer program stored in a computer-readable medium.

Although a few exemplary embodiments have been shown and described, it will be appreciated by those skilled in the art that changes may be made in these exemplary embodiments without departing from the principles and spirit of the invention, the scope of which is defined in the appended claims and their equivalents.

What is claimed is:

1. A display apparatus comprising:
   a camera configured to capture at least one image of a user;
   a storage configured to store information about stress areas on a body in accordance with corresponding postures of the user; and
   a processor configured to determine a posture of the user from the at least one image captured by the camera, determine a position of one or more stress areas on the body corresponding to the determined posture based on the stored information about the one or more stress areas on the body, and process a stress-related image, in which the determined one or more stress areas are marked on an image corresponding to a figure of the user; and
   a display configured to display the stress-related image, wherein the processor is further configured to, if it is determined that the user maintains in one posture over a predetermined time based on the at least one image captured by the camera, change a displaying status of the one or more stress areas in the stress-related image.

2. The display apparatus according to claim 1, wherein:
   the storage is further configured to store information about one or more relaxing areas on the body in accordance with the corresponding postures; and
   the processor is further configured to process the one or more stress areas and the one or more relaxing areas to be marked on the stress-related image.

3. The display apparatus according to claim 2, wherein the processor is further configured to process the one or more stress areas and the one or more relaxing areas to be different in color on the stress-related image.

4. The display apparatus according to claim 2, wherein the processor is further configured to process the one or more stress areas and the one or more relaxing areas to be different in contrast on the stress-related image.

5. The display apparatus according to claim 2, wherein the processor is further configured to process the one or more stress areas and the one or more relaxing areas to be different in brightness on the stress-related image.

6. The display apparatus according to claim 1, wherein the display is further configured to display a content image corresponding to a predetermined content together with the stress-related image.

7. The display apparatus according to claim 6, wherein the processor is further configured to determine the posture of the user while the content image is being displayed.

8. The display apparatus according to claim 6, wherein the processor is further configured to adjust the one or more stress areas in the stress-related image to become larger as time elapses while the user stays in one posture, and return the one or more stress areas in the stress-related image to an original size if it is determined that the user changes the posture while the one or more stress areas in the stress-related image is enlarged.

9. The display apparatus according to claim 1, wherein the processor is further configured to process the one or more stress areas to be expanded on the stress-related image as time elapses while the user stays in one posture.

10. A method of controlling a display, the method comprising:
    capturing at least one image of a user with a camera;
    determining a posture of the user from the at least one image captured by the camera, and determining a position of one or more stress areas on a body corresponding to the determined posture based on information previously stored about the one or more stress areas on the body, in accordance with corresponding postures of the user;
    displaying a stress-related image, in which the determined one or more stress areas are marked on an image corresponding to a figure of the user, on the display; and
    if it is determined that the user maintains in one posture over a predetermined time based on the at least one image captured by the camera, changing a displaying status of the one or more stress areas in the stress-related image.

11. The method according to claim 10, wherein:
    the determining the one or more stress areas on the body corresponding to the determined posture further comprises determining one or more relaxing areas on the body corresponding to the determined posture based on information previously stored about the one or more relaxing areas on the body in accordance with the corresponding postures; and the displaying the stress-related image comprises displaying the one or more stress areas and the one or more relaxing areas on the stress-related image.

12. The method according to claim 11, wherein the displaying the one or more stress areas and the one or more relaxing areas comprises displaying the one or more stress areas and the one or more relaxing areas to be different in color on the stress-related image.

13. The method according to claim 11, wherein the displaying the one or more stress areas and the one or more relaxing areas comprises displaying the one or more stress areas and the one or more relaxing areas to be different in contrast on the stress-related image.

14. The method according to claim 11, wherein the displaying the one or more stress areas and the one or more relaxing areas comprises displaying the one or more stress areas and the one or more relaxing areas to be different in brightness on the stress-related image.

15. The method according to claim 10, further comprising displaying a content image corresponding to a predetermined content, and
wherein the displaying the stress-related image comprises displaying the stress-related image together with the content image.

16. The method according to claim 15, wherein the determining the posture of the user comprises determining the posture of the user while the content image is being displayed.

17. The method according to claim 15, wherein the changing the displaying status of the one or more stress areas comprises:
adjusting the one or more stress areas in the stress-related image to become larger as time elapses while the user stays in one posture; and
returning the one or more stress areas in the stress-related image to an original size if it is determined that the user changes the posture while the one or more stress areas in the stress-related image is enlarged.

18. The method according to claim 10, wherein the changing the displaying status of the one or more stress areas comprises expanding the one or more stress areas on the stress-related image as time elapses while the user takes one posture.

* * * * *